United States Patent
Luscher

(10) Patent No.: US 9,226,827 B2
(45) Date of Patent: Jan. 5, 2016

(54) POROUS METAL STRUCTURES MADE FROM POLYMER PREFORMS

(75) Inventor: Patrik Luscher, Pfaffikon (CH)

(73) Assignee: Zimmer GmbH, Winterthur (CH)

( * ) Notice: Subject to any disclaimer, the term of this patent is extended or adjusted under 35 U.S.C. 154(b) by 151 days.

(21) Appl. No.: 13/885,303

(22) PCT Filed: Nov. 16, 2011

(86) PCT No.: PCT/EP2011/005773
§ 371 (c)(1),
(2), (4) Date: Aug. 7, 2013

(87) PCT Pub. No.: WO2012/065729
PCT Pub. Date: May 24, 2012

(65) Prior Publication Data
US 2013/0310948 A1    Nov. 21, 2013

(30) Foreign Application Priority Data

Nov. 17, 2010   (EP) .................................... 10014692

(51) Int. Cl.
*A61F 2/28* (2006.01)
*A61B 17/68* (2006.01)
(Continued)

(52) U.S. Cl.
CPC . *A61F 2/28* (2013.01); *A61B 17/68* (2013.01); *A61B 17/866* (2013.01); *A61C 8/0012* (2013.01); *A61C 8/0013* (2013.01); *A61C 8/0016* (2013.01); *A61C 13/0003* (2013.01); *A61F 2/30756* (2013.01); *A61F 2/389* (2013.01); *A61F 2/4241* (2013.01); *A61L 27/306* (2013.01); *A61L 27/56* (2013.01); *A61F 2/3094* (2013.01); *A61F 2/30907* (2013.01); *A61F 2002/30011* (2013.01);
(Continued)

(58) Field of Classification Search
CPC .................................. A61L 31/10; A61F 2/28
USPC .................... 623/16.11, 18.11, 23.51–23.61; 427/2.24
See application file for complete search history.

(56) References Cited

U.S. PATENT DOCUMENTS 3,109,712 A    11/1963  Redfern
4,022,875 A *  5/1977   Vinton et al. ............. 423/445 R
(Continued)

FOREIGN PATENT DOCUMENTS

WO    WO-02066693 A1    8/2002
WO    WO-2009097412 A2  8/2009
WO    WO-2012065729 A1  5/2012

OTHER PUBLICATIONS

"European Application Serial No. 10014692.7, European Search Report mailed Apr. 8, 2011", 3 pgs.
(Continued)

*Primary Examiner* — Jason-Dennis Stewart
(74) *Attorney, Agent, or Firm* — Schwegman Lundberg & Woessner, P.A.

(57) ABSTRACT

The present disclosure relates to porous orthopedic implants made from polymer preforms and a method of manufacturing the same. A polymer material may be formed into a preform, such as by an injection molding process or an additive manufacturing process. In an exemplary embodiment, the overall shape and the porous framework of the preform is predetermined to be substantially the same as the overall shape and the porous framework of the final orthopedic implant. Then, the preform may be pyrolyzed and coated with metal to form the final orthopedic implant.

15 Claims, 6 Drawing Sheets

(51) Int. Cl.
*A61B 17/86* (2006.01)
*A61C 8/00* (2006.01)
*A61C 13/00* (2006.01)
*A61F 2/30* (2006.01)
*A61F 2/38* (2006.01)
*A61F 2/42* (2006.01)
*A61L 27/30* (2006.01)
*A61L 27/56* (2006.01)

(52) U.S. Cl.
CPC ............... *A61F 2002/3092* (2013.01); *A61F 2002/30841* (2013.01); *A61F 2002/30884* (2013.01); *A61F 2002/30899* (2013.01); *A61F 2002/30962* (2013.01); *A61F 2002/30973* (2013.01); *A61F 2002/30981* (2013.01); *A61F 2002/30985* (2013.01)

(56) References Cited

U.S. PATENT DOCUMENTS

| | | | |
|---|---|---|---|
| 4,067,956 A * | 1/1978 | Franklin et al. | 423/445 R |
| 5,282,861 A | 2/1994 | Kaplan | |
| 6,103,149 A | 8/2000 | Stankiewicz | |
| 6,974,625 B2 | 12/2005 | Hunter et al. | |
| 2009/0062821 A1* | 3/2009 | Johnson et al. | 606/151 |
| 2009/0240337 A1* | 9/2009 | Myung et al. | 623/18.11 |
| 2011/0202142 A1* | 8/2011 | Mao et al. | 623/23.72 |

OTHER PUBLICATIONS

"International Application Serial No. PCT/EP2011/005773, International Search Report mailed Apr. 5, 2012", 3 pgs.

"Australian Application Serial No. 2011331500, Australian Patent Examination Report mailed Mar. 25, 2015", 5 pgs.

"International Application Serial No. PCT/EP2011/005773, International Preliminary Report on Patentability mailed Nov. 20, 2012", 16 pgs.

"International Application Serial No. PCT/EP2011/005773, Written Opinion mailed Apr. 5, 2012", 5 pgs.

"Wikipedia: Glassy Carbon", [Online]. [Archived Mar. 19, 2015]. Retrieved from the Internet: <URL: http://en.wikipedia.org/wiki/Glassy_carbon>, (Mar. 19, 2015), 6 pgs.

Mercuri, R. A, et al., "Carbon foam: its preparation and properties", Journal of American Chemical Society, Division of Fuel Chemistry vol. 12(4), (1968), 103-108.

* cited by examiner

POROUS METAL STRUCTURES MADE FROM POLYMER PREFORMS

CLAIM OF PRIORITY

This application is a U.S. National Stage Filing under 35 U.S.C. 371 from International Application No. PCT/EP2011/005773, filed on Nov. 16, 2011, and published as WO 2012/065729 A1 on May 24, 2012, which claims the benefit of European Application Serial No. 10014692.7, filed on Nov. 17, 2010, which applications and publications are incorporated herein by reference in their entirety.

BACKGROUND

1. Field of the Invention

The present invention relates to porous orthopedic implants. More particularly, the present invention relates to porous orthopedic implants made from polymeric preforms, and to a method of manufacturing the same.

2. Description of the Related Art

Orthopedic implants may be constructed of porous biomaterial to encourage bone growth into the orthopedic implant. An example of such a material is produced using Trabecular Metal™ technology generally available from Zimmer, Inc., of Warsaw, Ind. Trabecular Metal™ is a trademark of Zimmer, Inc. Such a material, which is also referred to as "TM" in the following, may be formed from a reticulated vitreous carbon (RVC) foam substrate which is infiltrated and coated with a biocompatible metal in the manner disclosed in detail in U.S. Pat. No. 5,282,861 to Kaplan, the disclosure of which is expressly incorporated herein by reference. The resulting, coated material is lightweight, strong, and has open cells that resemble the structure of natural cancellous bone, thereby providing a matrix into which cancellous bone may grow to fix the orthopedic implant to the patient's bone.

The starting material in this process is an open-cell polymer foam block or sheet. Polymer foams may be made by the controlled expansion of gas during the polymerization process. Standard polyurethane, for example, is made by reacting polyisocyanates and polyols. Polyurethane foam, on the other hand, is typically made by reacting polyisocyanates, polyols, and additionally a blowing agent, such as water. During the polymerization process, the water reacts to form carbon dioxide gas that expands and escapes from the surrounding polyurethane, leaving behind open cells surrounded by polyurethane ligaments.

The polymer foam starting material is then converted into an RVC foam substrate. This step may involve first impregnating the polymer foam with a carbonaceous resin and then heating the impregnated foam to a suitable pyrolysis temperature, on the order of 800° C. to 2000° C., to convert the polymer foam and any carbonaceous resin into vitreous carbon. This process is described in U.S. Pat. No. 6,103,149 to Stankiewicz, the disclosure of which is expressly incorporated herein by reference. The RVC foam substrate is then infiltrated and coated with a biocompatible metal, as discussed above.

Using an open-cell polymer foam as the starting material for a porous orthopedic implant presents certain challenges.

First, achieving the desired, final shape of the orthopedic implant may be difficult, because polymer foams are typically provided in blocks or sheets that must be machined at some point in the process into the desired, final shape. For example, the component may be machined while in the polymer foam form, the RVC foam form, or the coated metal form. Such machining is both expensive and time-consuming. Also, such machining may damage the ligaments that define the open-cell pores of the foam, especially when the component is shaped while in the brittle, RVC foam form. Finally, such machining is wasteful, because scraps from the bulk blocks or sheets may have to be discarded.

Second, the minimum thickness of the porous orthopedic implant is limited. In general, the porous orthopedic implant must be at least as thick as several supporting polymer ligaments, which may be about 0.5 mm in length each. Therefore, it can be difficult to manufacture small implants, such as dental implants and orthopedic fasteners, with a process based on polymer foam.

Third, polymer foam is entirely porous. Therefore, polymer foam does not provide non-porous regions, which may be desirable in an orthopedic implant.

SUMMARY

The present invention provides porous orthopedic implants made from polymer preforms and a method of manufacturing the same. A polymer material may be formed into a preform, such as by an injection molding process or an additive manufacturing process. In an exemplary embodiment, the overall shape and the porous framework of the preform may be substantially the same as the overall shape and the porous framework of the final orthopedic implant. Then, the preform may be pyrolyzed and coated with metal to form the final orthopedic implant.

The present invention presents a new concept which makes it possible to manufacture porous material and/or porous parts, such as porous implants. In an example, specifically designed reticulated polymer structures may be used as the basis for new implant types. Any suitable starting material, including currently used PUR foams, may be used. Such reticulated structures may be manufactured from polymer by state of the art rapid manufacturing or injection molding technologies, for example. These polymer pre-shapes or preforms may be exact oversize skeletons of the later implant component and may define both outer shape and internal structure. If applied, a subsequent pyrolyzing step may involve a considerable but uniform and predictable shrinkage to the size of the final implant which facilitates a highly reproducible manufacturing process. CVD coating by tantalum, as for example applied in current manufacturing, may complete the process.

The coating step may comprise performing a chemical vapor deposition process to deposit metal onto the preform and/or infiltrating the pores to deposit metal onto the plurality of ligaments of the preform.

The plurality of ligaments may exhibit substantially isotropic growth during the coating step.

According to an aspect of the present invention, a method is provided for manufacturing a porous orthopedic implant. The method includes the steps of: forming a polymeric preform in a three-dimensional geometric shape that is substantially the same as the three-dimensional geometric shape of the orthopedic implant, the preform including a plurality of ligaments defining pores therebetween; pyrolyzing the preform; and coating the preform with metal to produce the orthopedic implant.

According to another aspect of the present invention, a method is provided for manufacturing a porous orthopedic implant. The method includes the steps of: forming a polymeric preform having a substantially final shape that is suitable for implantation into a patient's body, the preform including a plurality of ligaments defining pores therebetween; pyrolyzing the preform; and coating the preform with metal to produce the orthopedic implant.

According to another aspect of the present invention, a method is provided for manufacturing a porous orthopedic implant. The method includes the steps of: forming a plurality of polymeric ligaments, each ligament having a predetermined location, a predetermined size, and a predetermined shape, the plurality of ligaments defining pores therebetween, the plurality of ligaments cooperating to define at least a portion of a preform; and coating the preform with metal to produce the orthopedic implant. In this method, as well as in other methods according to the present invention, a step of pyrolyzing the preform may or may not be carried out.

The present invention also relates to porous implants which are obtained or obtainable by a method according to the present invention. While in the related art as discussed above the machining, to obtain the desired three-dimensional geometric shape, is carried out after the pyrolyzing step so that the implant exhibits characteristic, identifiable properties caused by the machining, the implants according to the present invention do not exhibit such properties. Thus, the nonexistence of such properties makes it possible to distinguish implants according to the present invention from implants according to the related art as discussed above.

According to an aspect, in an implant according to the present invention, the ligaments may exhibit a spatial structure being different from a random spatial structure. In particular, the spatial structure of the ligaments may be such that the implant has at least one of (i) an anisotropic and/or locally varying structure, (ii) anisotropic and/or locally varying mechanical properties, (iii) an anisotropic and/or locally varying porosity, and (iv) mechanical properties being dependent on the direction of an externally applied load. Thus, this non-random spatial structure makes it possible to distinguish implants according to the present invention from implants according to the related art as discussed above.

The non-random spatial structure of the ligaments can be specifically designed as desired. Thus, not only the three-dimensional geometric shape of the implant but also its surface properties and/or its inner structure can be designed and thus predetermined as desired.

The term "spatial structure" as used herein may relate to the spatial distribution, the location, the size and/or the orientation of the ligaments and/or of the pores defined by the ligaments.

Additionally or alternatively, an implant according to the present invention may, by way of example only, be distinguished from implants according to the related art as discussed above by having, at least partly, (i) a specific, finely formed geometric shape with relatively small dimensions, (ii) regions with different porosities, in particular including one or more non-porous regions, and/or (iii) anisotropic mechanical properties.

The present invention has various advantages, some of them being mentioned in the following by way of example only. Generally, the present invention does not require a machining after the pyrolyzing step as discussed above in connection with the related art. Rather, the preform obtained in the forming step does already have the three-dimensional geometric shape of the orthopedic implant. Another advantage is that the minimum dimensions, such as the minimum thickness, of the orthopedic implant are/is no longer limited. A further advantage is that the orthopedic implant can be provided with non-porous regions. In addition, with the present invention it is possible to manufacture orthopedic implants having a non-isotropic porosity or—more generally—non-isotropic properties. Moreover, the present invention allows to make use of a variety of methods, including established methods, for making the preform.

The present invention may facilitate the use of polymeric mass production processes for producing porous parts instead of machining each part individually from previously pyrolized material. Thus, the manufacturing costs may be considerably lowered. Further, the present invention allows to design totally new features on implants, for example two-dimensional structures, small fixation elements and connectors to instruments. Moreover, the present invention allows to produce porous parts and features which are smaller than currently possible. In addition, the present invention allows to specifically design the material structure which may also be anisotropic. Therefore, it is possible to optimize the mechanical properties of the orthopedic implant according to its intended use. Furthermore, the present invention allows the manufacturing of hollow bodies from porous material.

Consequently, the technology according to the present invention may open up a wide range of new design options. For example, small implants from porous tantalum structures (e.g. screws or dental implants) may be manufactured. Currently, such structures are difficult to design in a reliable manner since the strut size of the currently available TM structures approaches the implant dimensions. Further, unique fixation elements such as special threads or retroserrated elements may be produced. In addition, it is possible to manufacture implants having non-isotropic and/or locally variable mechanical properties and/or porosities. Specifically, these implants may be tailored to a specific application (e.g. cages). In another example, porous, osseointegrating supports for hydrogel or soft polymer cartilage replacement materials with a barrier layer against creep of the hydrogel/polymer into the porous structure may be manufactured. Moreover, the invention allows to manufacture hollow bodies with porous walls. According to another example, porous tantalum structures with integrated instrument adapters (e.g. hexagon sockets) may be produced. Further, it is possible to produce components from porous tantalum with decreased (implantation) or increased (primary fixation) surface roughness as compared to the currently available TM material. As an additional aspect, the present invention allows to provide fancy visual effects.

As used herein, the term "orthopedic implant" may refer to the final implant suitable for implantation into a patient's body. Alternatively, the "orthopedic implant" may be only a part of the final implant. The final implant may consist of or comprise only one orthopedic implant or a plurality of, i.e. at least two, orthopedic implants which need not all be made from a porous material. The term "preform" as used herein may refer to a single preform or to a plurality of, i.e. at least two, preforms each of which being formed according to the present invention and which are coupled together or connected to each other to form a "combined preform" for further processing. The terms "porous material" or "porous part" as used herein are meant to comprise a material or part, respectively, which is coated, in particular coated with metal, as well as which is not coated. If coated with metal, the material or part, respectively, is also referred to herein as "porous metal or metallic material", "porous metal or metallic part" or "porous metal or metallic structure".

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
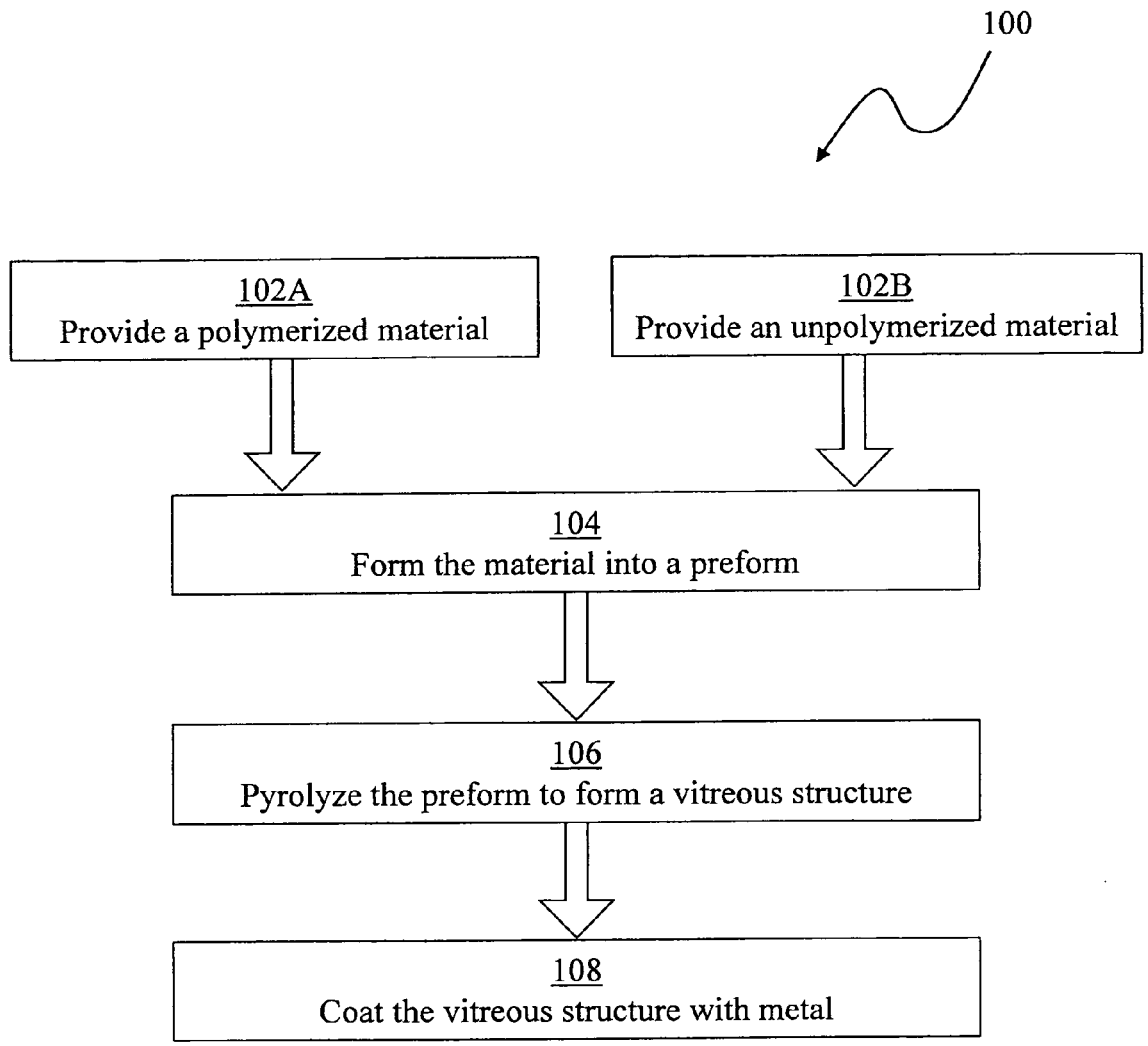
FIG. 1 is a flow diagram of an exemplary method of the present invention.

FIG. 1 provides an exemplary method 100 for manufacturing a porous orthopedic implant.

Beginning at step 102A of method 100, a polymerized material is provided. The polymerized material provided in step 102A may be polyurethane, polystyrene, polypropylene, polyethylene, polyoxymethylene, or another suitable polymer, that has already been polymerized. For example, polyisocyanates and polyols may be reacted in an earlier step to provide fully polymerized polyurethane in step 102A. The polymerized material provided in step 102A may be in an unformed condition, such as in a molten state or a powdered state, for example.

Alternatively, at step 102B of method 100, a material may be provided that has not yet been fully polymerized, and polymerization may occur during subsequent processing steps. In this embodiment, the unpolymerized material may include the reactants for producing a polymer, such as polyisocyanates and polyols.

Continuing to step 104 of method 100, the polymerized material from step 102A or the unpolymerized material from step 102B is formed into a preform having a desired, substantially final shape, both internally and externally. For example, the forming step 104 may produce a preform in a substantially final shape that is suitable for implantation in the body as is, without requiring subsequent machining. When a polymerized material is provided that has already been polymerized (step 102A), the forming step 104 may occur without further polymerization of the polymerized material. Alternatively, when an unpolymerized material is provided (step 102B), polymerization may occur during the forming step 104.

Figure 11:
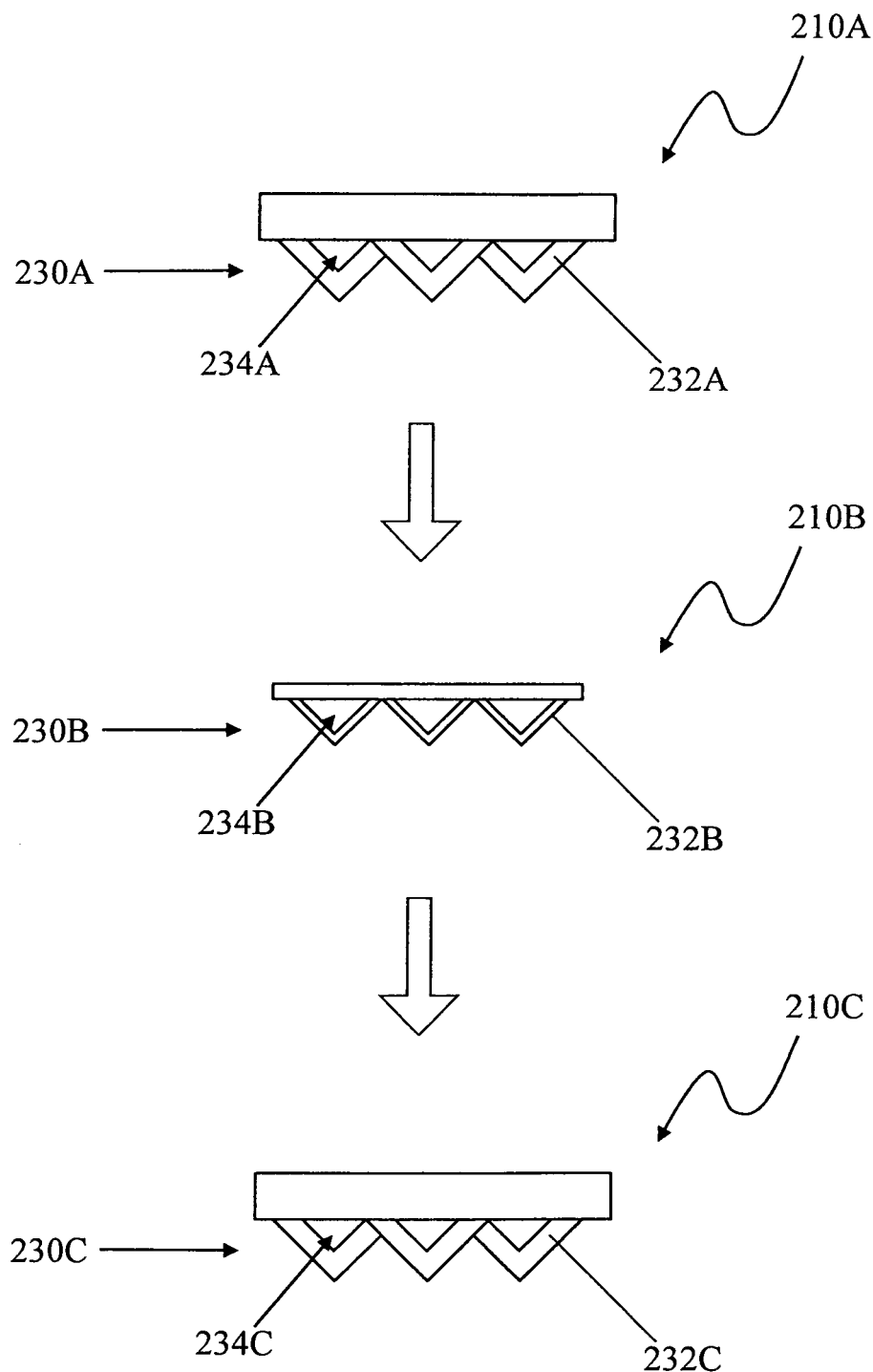
FIG. 11 is a schematic diagram of an exemplary method of the present invention.

With reference to FIG. 11, a preform 210A formed during step 104 is illustrated schematically. At least a portion of the polymeric preform 210A formed during step 104 is porous and may include an interconnected network of open cells or pores 234A. Internally, the forming step 104 may involve forming the porous framework 230A of the preform 210A by forming a plurality of ligaments 232A, each ligament 232A having a predetermined shape, size, and location to, in turn, control the shape, size, and location of the pores 234A defined between the ligaments 232A. As used herein, forming each ligament 232A in a "predetermined" shape, size, and location means that each ligament 232A is designed to have a particular shape, size, and location, as opposed to a random shape, size, and location that one would get when using a blowing agent, for example. Because each ligament 232A may be designed to have a particular shape, size, and location, each pore 234A between the ligaments 232A may also be designed to have a particular shape, size, and location, as opposed to a random shape, size, and location that one would get when using a blowing agent, for example. Externally, the forming step 104 may involve forming the overall, three-dimensional geometric shape of the preform 210A.

According to an exemplary embodiment of the present invention, and with reference to FIG. 1, the preform formed during the forming step 104 is a near-net-shape or net-shape of the final orthopedic implant, both internally and externally. Therefore, the overall shape and the porous framework of the preform may be predetermined to be the same as or substantially the same as the overall shape and the porous framework of the final orthopedic implant, and little or no internal or external machining may be required to arrive at the overall shape and the porous framework of the final orthopedic implant. It is within the scope of the present invention that the size of the preform may differ from the size of the final orthopedic implant to account for uniform shrinkage and growth that occurs during subsequent processing steps, as discussed below.

An exemplary method for forming the preform in step 104 of method 100 is an injection molding process. Injection molding may involve injecting a molten polymerized material from the providing step 102A into a mold cavity where it cools and hardens to the configuration of the mold cavity. Alternatively, injection molding may involve injecting reactants from the providing step 102B into a mold, where the reactants react to form a polymer and then harden to the configuration of the mold cavity. In this embodiment, the mold may define both the overall shape and the porous framework of the preform, so that the pores defined between individual ligaments have a particular shape, size, and location. Alternatively, the mold may define the overall shape of the preform, with the porous framework being formed randomly with the use of a blowing agent or a chemical reactant, for example.

Another exemplary method for forming the preform in step 104 of method 100 is an additive or rapid manufacturing process. Additive or rapid manufacturing involves laying down the polymer material layer by layer to build the final structure. Additive manufacturing processes may be distinguished from subtractive manufacturing processes, in which material is machined away from a bulk structure to arrive at the final structure.

A first exemplary type of additive or rapid manufacturing is 3-D printing, also known as stereolithography. 3-D printing involves feeding a liquid photopolymer through a nozzle to form a single cross-sectional layer of the final structure, and then exposing the photopolymer to a UV laser light to solidify the liquid photopolymer and to adhere the solidified layer onto the adjacent layer beneath. Then, a new liquid photopolymer layer is applied on top of the solidified layer, and the process is repeated until the final structure is completed. Alternatively, the UV laser light may be exposed to certain portions of a photopolymer vat to selectively harden only those portions of the photopolymer vat. Then, the hardened material may be submerged in the photopolymer vat and the process repeated to form a new layer on top of the hardened layer.

A second exemplary type of additive or rapid manufacturing is selective laser sintering. Selective layer sintering involves exposing certain portions of a polymer powder bed to a laser to selectively fuse together those portions of the powder and to adhere the sintered layer onto the adjacent layer beneath. Then, a new powder layer is applied on top of the sintered layer, and the process is repeated until the final structure is completed.

A third exemplary type of additive or rapid manufacturing is fused deposition modeling. Fused deposition modeling involves laying down small, extruded beads of a polymer material layer by layer to build the final structure. The polymer material may harden soon or immediately after it is extruded to adhere adjacent beads together and to adhere the extruded layer onto the adjacent layer beneath.

The above-described additive or rapid manufacturing processes for forming the preform in step 104 of method 100 present certain advantages over using polymer foam as the starting material. First, the above-described methods enable construction of complex structures, including structures having both porous and non-porous regions, hollow structures, and structures with integrated instrument connectors (e.g. sockets) designed to take up loads from an instrument or tool. Also, the above-described methods allow for mass part production of substantially final shapes without having to machine each individual part into its final shape, as is currently required when using bulk blocks of polymer foam. Therefore, the construction process may be shorter and less expensive than when using polymer foam. Additionally, the above-described methods facilitate construction of small structures, such as dental implants or orthopedic fasteners. As discussed above, polymer foam is limited by the size of its supporting polymer ligaments, but the porous framework of the polymer preforms of the present invention may not have such restrictive size limitations. Also, the porous framework (e.g. pore shape, pore size) of the polymer preform may be customized and may vary within the preform. For example, the bone-contacting surface of the polymer structure may be more porous than other portions of the polymer structure. Finally, the above-described methods enable construction of structures having anisotropic mechanical properties that may be customized depending on the intended use of the final orthopedic implant.

Another exemplary method for forming the preform in step 104 of method 100 is cutting or otherwise working the preform out of a suitable starting material.

After the forming step 104 of method 100, any excess material may be machined away or otherwise removed from the preform. Also, material may be added to the preform after the forming step 104. For example, a first portion of the preform and a second portion of the preform may be shaped separately during the forming step 104, and then the first portion and the second portion may be adhered or otherwise coupled together to make the preform.

Next, at step 106 of method 100 (FIG. 1), the polymer preform is pyrolyzed. This pyrolysis step 106 involves heating the polymer preform to a suitable pyrolysis temperature, on the order of 800° C. to 2000° C., in a low-oxygen or oxygen-free environment. Optionally, before heating, the polymer preform may be impregnated with a carbonaceous resin. Heating the polymer preform converts the polymer preform and any carbonaceous resin into "glassy" or "vitreous" carbon to form a reticulated vitreous carbon (RVC) structure. An exemplary pyrolysis process is described in the above-incorporated U.S. Pat. No. 6,103,149 to Stankiewicz. Another exemplary pyrolysis process is described in the U.S. Pat. No. 4,022,875 to Vinton et al., the disclosure of which is expressly incorporated herein by reference.

Optionally, the polymer preform may be cross-linked before the pyrolysis step 106. A cross-linked polymer preform may maintain its shape when subjected to the elevated temperatures of the pyrolysis step 106. The starting material (step 102) or the polymer preform (step 104) may be cross-linked by irradiation or with crosslinking reagents, for example.

The pyrolysis step 106 may cause shrinking of the polymer preform, this shrinking being in particular a uniform, isotropic shrinking. For example, the preform may shrink in dimension, i.e. linearly, by 5%, 10%, 15%, 20%, 25%, 30%, 35% or more during the pyrolysis step 106. To accommodate shrinking during the pyrolysis step 106, the forming step 104 may involve forming a polymer preform that is larger than the final orthopedic implant. The amount of shrinking may depend, amongst others, from the starting material and/or from the specific manner in which the method is carried out, e.g. from certain process parameters such as temperature, pressure, time etc.

Returning to FIG. 11, an RVC structure 210B formed during the pyrolysis step 106 is illustrated schematically. The RVC structure 210B is substantially the same geometric shape as the polymeric preform 210A. However, the RVC structure 210B is smaller in scale than the polymeric preform 210A due to uniform, isotropic shrinkage of each ligament 232B.

Finally, at step 108 of method 100 (FIG. 1), the RVC structure is infiltrated and coated with a biocompatible metal. Suitable biocompatible metals include, for example, tantalum, titanium, niobium, hafnium, tungsten, and alloys thereof. Although the preform may shrink during the pyrolysis step 106, the RVC structure may grow uniformly during the coating step 108 as metal is deposited onto the RVC structure. The growth from the coating step 108 may counteract some of the shrinkage from the pyrolysis step 106, but it may still be necessary to form a polymer preform during the forming step 104 that is larger than the final orthopedic implant. Alternatively, the growth from the coating step 108 may be more significant than the shrinkage from the pyrolysis step 106, so it may be necessary to form a polymer preform during the forming step 104 that is smaller than the final orthopedic implant.

An exemplary method for coating the RVC structure in step 108 of method 100 is a chemical vapor deposition (CVD) process. An exemplary CVD process is described in the above-incorporated U.S. Pat. No. 5,282,861 to Kaplan. During the coating step 108, the RVC structure may be placed inside a furnace and heated to a temperature of approximately 1100° C. Then, the RVC structure may be exposed to gaseous tantalum chloride ($TaCl_5$) and gaseous hydrogen ($H_2$), which react to produce solid tantalum metal. The resulting tantalum metal is then deposited onto the RVC structure to form a thin, uniform film of tantalum on the RVC structure. To promote even metal infiltration and deposition, the RVC structure may be flipped and/or rotated during the CVD process.

Returning to FIG. 11, a coated metal structure 210C formed during the coating step 108 is illustrated schematically. The coated metal structure 210C is substantially the same geometric shape as the RVC structure 210B. However, the coated metal structure 210C is larger in scale than the RVC structure 210B due to substantially uniform, isotropic metal deposition onto ligaments 232C.

After step 108 of method 100 (FIG. 1), the coated metal structure may be subjected to any necessary shaping, processing, sterilizing, or packaging steps. For example, a polymeric bearing component may be secured onto the coated metal structure to form an articulating, joint replacement implant. As another example, the coated metal structure may be coupled to a solid metal substrate, such as by sintering. In this embodiment, the coated metal structure may serve as a bone ingrowth region of the final implant.

Figure 2:
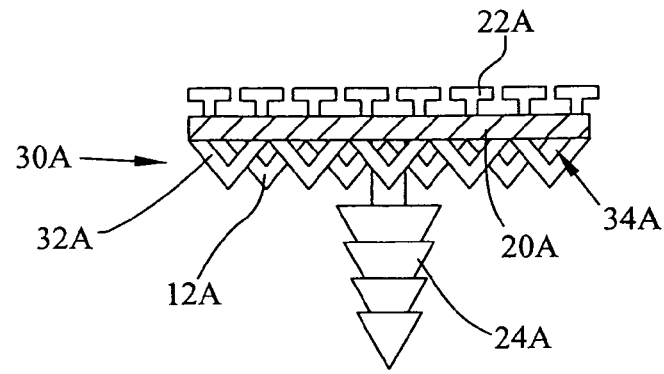
FIG. 2 is a partial cross-sectional view of a metallic supporting component of an exemplary cartilage replacement implant of the present invention.
Figure 3:
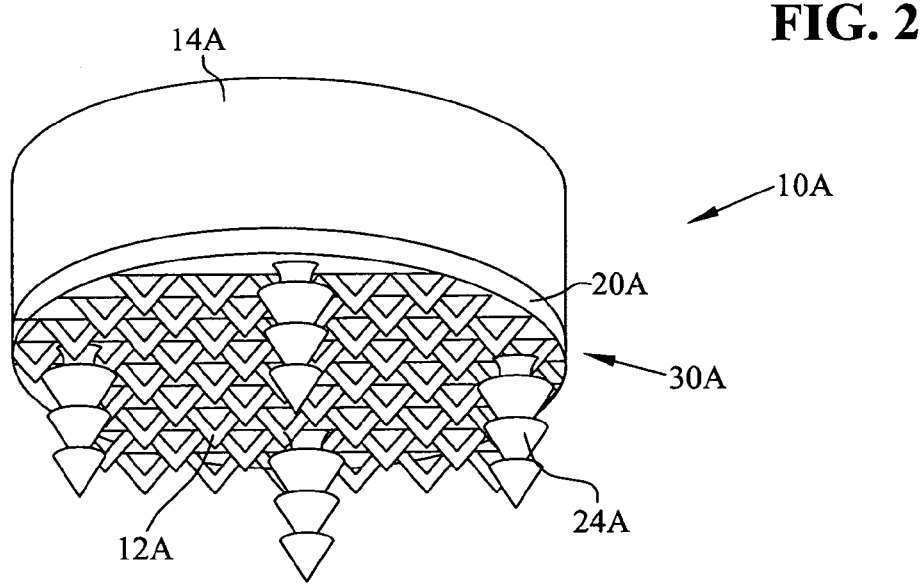
FIG. 3 is a perspective view of the metallic supporting component of FIG. 2, further including a polymeric bearing component attached thereto to form the cartilage replacement implant.
Figure 4:
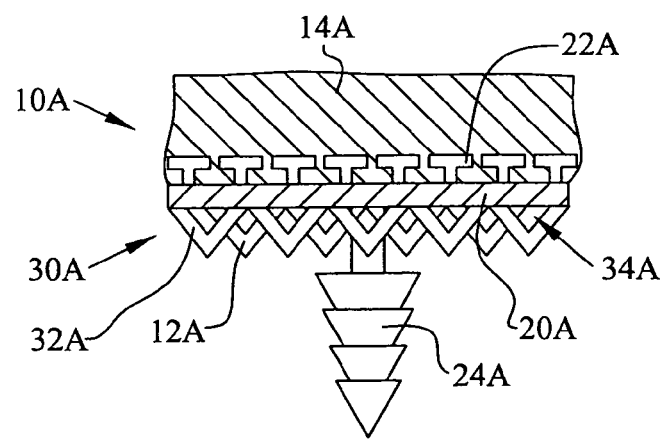
FIG. 4 is a partial cross-sectional view of the cartilage replacement implant of FIG. 3.

Referring to FIGS. 2-4, an exemplary orthopedic implant 10A is provided that may be formed according to the above-described method 100 (FIG. 1). Implant 10A may be used as a cartilage replacement implant. Alternatively, implant 10A may be used as part of a joint replacement system. For example, implant 10A may be used as a prosthetic tibial component.

Implant 10A includes a metallic supporting component 12A and a polymeric bearing component 14A. As shown in FIG. 2, metallic supporting component 12A of implant 10A includes base 20A, a plurality of attachment pins 22A, and a plurality of anchors 24A. Metallic supporting component 12A of implant 10A also includes a porous, bone-fixation region 30A that spans base 20A.

As shown in FIG. 4, attachment pins 22A extend upwardly from base 20A and into polymeric bearing component 14A to help secure polymeric bearing component 14A onto metallic supporting component 12A. Base 20A may serve as a barrier layer that supports polymeric bearing component 14A and prevents polymeric bearing component 14A from creeping into the porous, bone-fixation region 30A of metallic supporting component 12A. Base 20A may be a solid structure, or base 20A may be a punched or a grate-like structure having a plurality of holes. These holes may facilitate gas flow through implant 10A during the coating step 108 (FIG. 1) to ensure even coating of implant 10A. If the holes in the preform are small enough in size, the holes may be filled with metal during the coating step 108. In other words, base 20A of the preform may have holes, but base 20A of the final implant may lack holes.

Within porous, bone-fixation region 30A, implant 10A includes ligaments 32A defining open cells or pores 34A therebetween. Pores 34A of implant 10A provide a matrix into which cancellous bone may grow to fix implant 10A to the patient's bone. As shown in FIG. 3, anchors 24A extend downwardly from base 20A. With base 20A resting against the patient's bone, bone-fixation region 30A of implant 10A receives ingrown bone and anchors 24A extend downwardly into the patient's bone to anchor implant 10A in place.

Metallic supporting component 12A (FIG. 2) of implant 10A may be formed according to the above-described method 100 (FIG. 1). For example, a polymer preform that is identical or substantially identical in shape to metallic supporting component 12A may be formed by injection molding or by depositing a polymer material layer by layer, from anchors 24A, to base 20A, to attachment pins 22A, as set forth above with respect to step 104 of method 100 (FIG. 1). Then, the polymer preform may be pyrolyzed and coated with a biocompatible metal, as set forth above with respect to steps 106 and 108 of method 100 (FIG. 1), to form metallic supporting component 12A. Finally, polymeric bearing component 14A (FIGS. 3 and 4) may be attached to metallic supporting component 12A to arrive at the final implant 10A.

Figure 5:
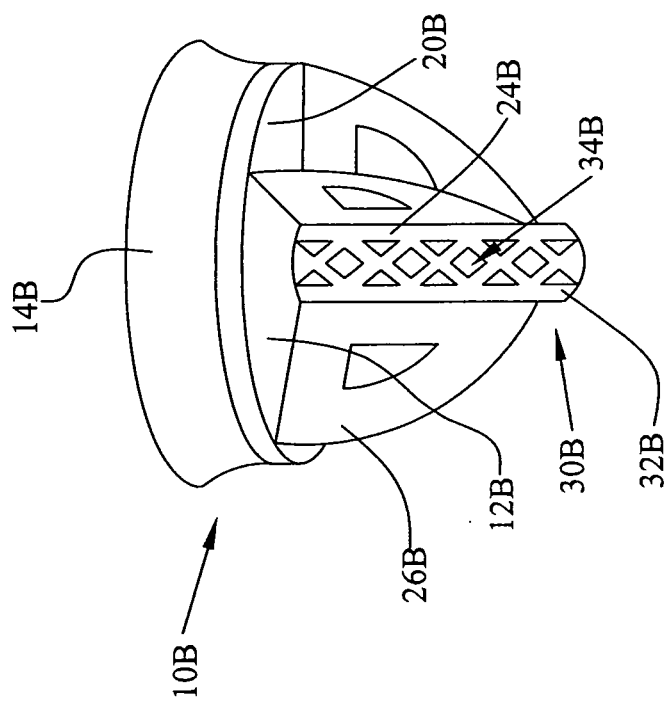
FIG. 5 is a perspective view of another exemplary cartilage replacement implant of the present invention, the cartilage replacement implant including a metallic supporting component and a polymeric bearing component.

Referring next to FIG. 5, another exemplary orthopedic implant 10B is provided that may be formed according to the above-described method 100 (FIG. 1). Implant 10B is similar to implant 10A (FIGS. 2-4), with like reference numerals identifying like elements. Implant 10B may be used as a cartilage replacement implant. Alternatively, implant 10B may be used as part of a joint replacement system. For example, implant 10B may be a used as a prosthetic tibial component.

Implant 10B includes a metallic supporting component 12B and a polymeric bearing component 14B. As shown in FIG. 5, metallic supporting component 12B of implant 10B includes base 20B, anchor 24B, and a plurality of ribs 26B extending radially from anchor 24B and generally diagonally between base 20B and anchor 24B. Implant 10B also includes a porous, bone-fixation region 30B that spans both base 20B and anchor 24B.

Within porous, bone-fixation region 30B, implant 10B includes ligaments 32B defining open cells or pores 34B therebetween. Pores 34B of implant 10B provide a matrix into which cancellous bone may grow to fix implant 10B to the patient's bone. As shown in FIG. 5, anchor 24B and ribs 26B extend downwardly from base 20B. With base 20B resting against the patient's bone, bone-fixation region 30B of implant 10B receives ingrown bone and anchor 24B and ribs 26B extend downwardly into the patient's bone to anchor implant 10B in place.

Metallic supporting component 12B of implant 10B may be formed according to the above-described method 100 (FIG. 1). For example, a polymer preform that is identical or substantially identical in shape to metallic supporting component 12B may be formed by injection molding or by depositing a polymer material layer by layer, from anchor 24B to base 20B, as set forth above with respect to step 104 of method 100 (FIG. 1). Then, the polymer preform may be pyrolyzed and coated with a biocompatible metal, as set forth above with respect to steps 106 and 108 of method 100 (FIG. 1), to form metallic supporting component 12B. Finally, polymeric bearing component 14B may be attached to metallic supporting component 12B to arrive at the final implant 10B.

Figure 6:
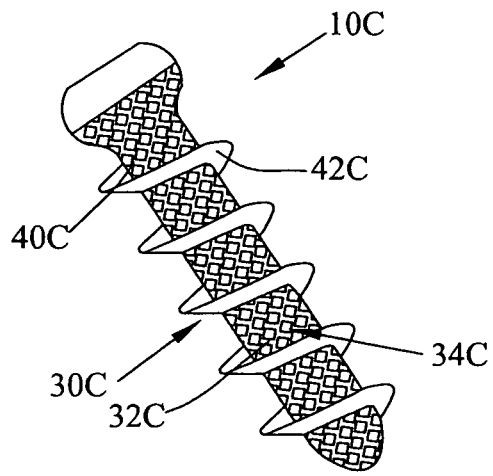
FIG. 6 is an elevational view of an exemplary orthopedic screw of the present invention.

Referring next to FIG. 6, another exemplary orthopedic implant 10C is provided that may be formed according to the above-described method 100 (FIG. 1). Implant 10C may be in the shape of a screw for use as an orthopedic fastener.

Implant 10C includes shaft 40C and thread 42C that surrounds shaft 40C. Implant 10C also includes a porous, bone-fixation region 30C that spans shaft 40C. Within porous, bone-fixation region 30C, implant 10C includes ligaments 32C defining open cells or pores 34C therebetween. Pores 34C of implant 10C provide a matrix into which cancellous bone may grow to fix implant 10C to the patient's bone.

Implant 10C may be formed according to the above-described method 100 (FIG. 1). For example, a polymer preform that is identical or substantially identical in shape to implant 10C may be formed by injection molding or by depositing a polymer material layer by layer, as set forth above with respect to step 104 of method 100 (FIG. 1). Then, the polymer preform may be pyrolyzed and coated with a biocompatible metal, as set forth above with respect to steps 106 and 108 of method 100 (FIG. 1), to form the final implant 10C.

Figure 7:
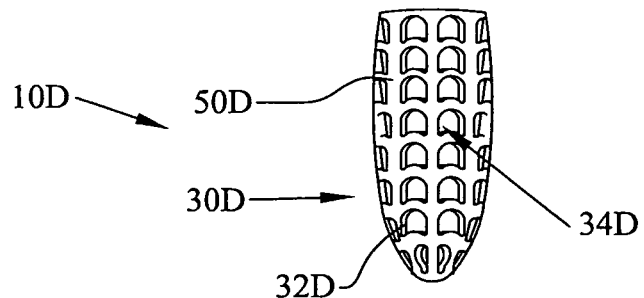
FIG. 7 is an elevational view of an exemplary dental implant of the present invention.

Referring next to FIG. 7, another exemplary orthopedic implant 10D is provided that may be formed according to the above-described method 100 (FIG. 1). Implant 10D may be used as a dental implant.

Implant 10D includes a generally hollow body 50D. Implant 10D also includes a porous, bone-fixation region 30D that spans body 50D. Within porous, bone-fixation region 30D, implant 10D includes ligaments 32D defining open cells or pores 34D therebetween. Pores 34D of implant 10D provide a matrix into which cancellous bone may grow to fix implant 10D to the patient's bone.

Implant 10D may be formed according to the above-described method 100 (FIG. 1). For example, a polymer preform that is identical or substantially identical in shape to implant 10D may be formed by injection molding or by depositing a polymer material layer by layer, as set forth above with respect to step 104 of method 100 (FIG. 1). Then, the polymer preform may be pyrolyzed and coated with a biocompatible metal, as set forth above with respect to steps 106 and 108 of method 100 (FIG. 1), to form the final implant 10D.

Figure 8:
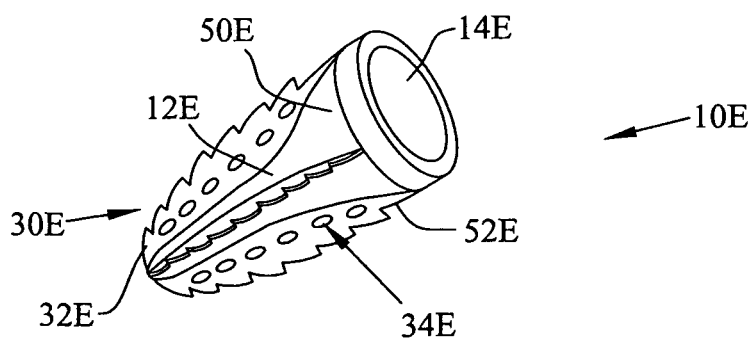
FIG. 8 is a perspective view of an exemplary finger implant of the present invention.

Referring next to FIG. 8, another exemplary orthopedic implant 10E is provided that may be formed according to the above-described method 100 (FIG. 1). Implant 10E may be used as a finger joint implant.

Implant 10E includes a metallic supporting component 12E and a polymeric bearing component 14E. Metallic supporting component 12E of implant 10E includes body 50E having sharp, flanged ribs 52E extending therefrom. Metallic supporting component 12E of implant 10E also includes a porous, bone-fixation region 30E that spans both body 50E and ribs 52E. Within porous, bone-fixation region 30E, implant 10E includes ligaments 32E defining open cells or pores 34E therebetween. Pores 34E of implant 10E provide a matrix into which cancellous bone may grow to fix implant 10E to the patient's bone.

Implant 10E may be formed according to the above-described method 100 (FIG. 1). For example, a polymer preform that is identical or substantially identical in shape to metallic supporting component 12E may be formed by injection molding or by depositing a polymer material layer by layer, as set forth above with respect to step 104 of method 100 (FIG. 1). Then, the polymer preform may be pyrolyzed and coated with a biocompatible metal, as set forth above with respect to steps 106 and 108 of method 100 (FIG. 1), to form metallic supporting component 12E. Finally, polymeric bearing component 14E may be attached to metallic supporting component 12E to arrive at the final implant 10E.

Figure 9:
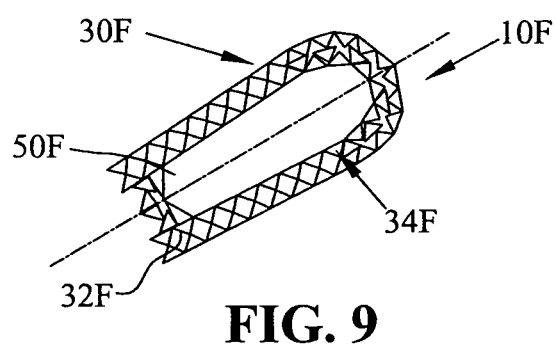
FIG. 9 is a cross-sectional view of an exemplary orthopedic rod of the present invention.
Figure 10:
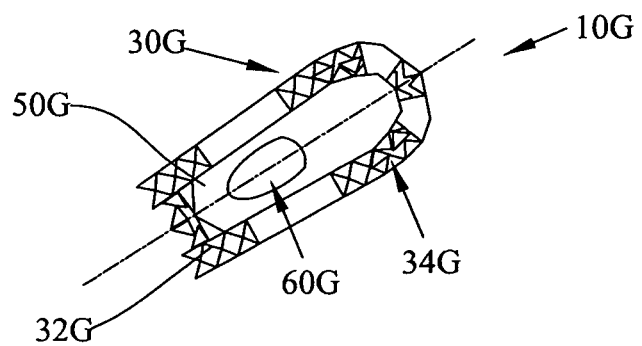
FIG. 10 is a cross-sectional view of another orthopedic rod of the present invention.

Referring finally to FIGS. 9 and 10, other exemplary orthopedic implants 10F, 10G, are provided that may be formed according to the above-described method 100 (FIG. 1). Implants 10F, 10G, may be rods used to treat avascular necrosis (AVN).

Implant 10F of FIG. 9 includes an elongate, generally hollow body 50F. Body 50F may provide mechanical support to avascular bone tissue and prevent articulating surfaces from collapsing. Implant 10F also includes a porous, bone-fixation region 30F that spans body 50F. Within porous, bone-fixation region 30F, implant 10F includes ligaments 32F defining open cells or pores 34F therebetween. Pores 34F of implant 10F provide a matrix into which cancellous bone may grow to fix implant 10F to the patient's bone. Pores 34F of implant 10F may also encourage a blood supply to build within the hollow body 50F and within the avascular bone tissue. As shown with respect to implant 10G of FIG. 10, the build-up of a blood supply may be further encouraged by the presence of macroscopic openings 600 in body 50G.

Implants 10F, 100, may be formed according to the above-described method 100 (FIG. 1). For example, a polymer preform that is identical or substantially identical in shape to implants 10F, 10G, may be formed by injection molding or by depositing a polymer material layer by layer, as set forth above with respect to step 104 of method 100 (FIG. 1). Then, the polymer preform may be pyrolyzed and coated with a biocompatible metal, as set forth above with respect to steps 106 and 108 of method 100 (FIG. 1), to form the final implants 10F, 10G.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A method of manufacturing a porous orthopedic implant comprising the steps of:
    forming a polymeric preform in a three-dimensional geometric shape that is substantially the same as the three-dimensional geometric shape of the orthopedic implant, the polymeric preform including a plurality of ligaments defining pores therebetween;
    after said forming the polymeric preform, pyrolyzing the polymeric preform; and
    after said pyrolyzing the polymeric preform, coating the pyrolyzed polymeric preform with metal to produce the orthopedic implant.

2. The method of claim 1, wherein the preform produced during the forming step and the orthopedic implant produced during the coating step differ in scale.

3. The method of claim 2, wherein the preform produced during the forming step is larger in scale than the orthopedic implant produced during the coating step to account for shrinkage of the plurality of ligaments during the pyrolyzing step.

4. The method of claim 1, wherein the forming step comprises injecting one of a polymer material and an unpolymerized material into a mold to form the preform,
    and/or wherein the forming step comprises performing a rapid manufacturing process to form the preform,
    and/or wherein the forming step comprises depositing a polymer material layer by layer to form the preform,
    and/or wherein the forming step comprises cutting the preform out of a starting material to form the preform.

5. The method of claim 1, wherein the forming step comprises separately forming a first portion of the preform and a second portion of the preform, the method further comprising the step of coupling the first and second portions of the preform together.

6. The method of claim 1, further comprising the step of providing an unformed polymer material before the forming step, wherein the forming step occurs without further polymerization of the polymer material,
    in particular wherein the unformed polymer material is in one of a powdered state and a molten state.

7. A porous orthopedic implant obtained by the method of claim 1.

8. The implant according to claim 7, wherein the method is carried out such that the ligaments exhibit a spatial structure being different from a random spatial structure, in particular wherein the spatial structure of the ligaments is such that the implant has at least one of (i) an anisotropic and/or locally varying structure, (ii) anisotropic and/or locally varying mechanical properties, (iii) an anisotropic and/or locally varying porosity, and (iv) mechanical properties being dependent on the direction of an externally applied load.

9. A method of manufacturing a porous orthopedic implant comprising the steps of:
   forming a polymeric preform having a substantially final shape that is suitable for implantation into a patient's body, the polymeric preform including a plurality of ligaments defining pores therebetween;
   after said forming the polymeric preform, pyrolyzing the polymeric preform; and
   after said pyrolyzing the polymeric preform, coating the pyrolyzed polymeric preform with metal to produce the orthopedic implant.

10. The method of claim 9, wherein the pyrolyzing step and the coating step alter the scale of the preform while substantially maintaining the final shape of the preform.

11. The method of claim 9, wherein the step of forming the preform does not include a machining.

12. The method of claim 9, wherein the forming step comprises forming each of the plurality of ligaments at a predetermined location, in a predetermined size, and in a predetermined shape.

13. The method of claim 9, further comprising the step of attaching a polymeric bearing layer to the orthopedic implant after the coating step.

14. A method of manufacturing a porous orthopedic implant comprising the steps of:
   forming a plurality of polymeric ligaments, each ligament having a predetermined location, a predetermined size, and a predetermined shape, the plurality of ligaments defining pores therebetween, the plurality of ligaments cooperating to define at least a portion of a preform;
   after said forming the plurality of polymeric ligaments, pyrolyzing the preform; and
   after said pyrolyzing the preform, coating the pyrolyzed preform with metal to produce the orthopedic implant.

15. The method of claim 14, wherein the forming step comprises performing at least one of stereolithography, selective laser sintering, and fused deposition modeling.

* * * * *